United States Patent [19]

Login

[11] Patent Number: 4,764,306

[45] Date of Patent: Aug. 16, 1988

[54] PROCESS FOR THE MANUFACTURE OF BIS-QUATERNARY AMMONIUM COMPOUNDS

[75] Inventor: Robert B. Login, Oakland, N.J.

[73] Assignee: PPG Industries, Inc., Pittsburgh, Pa.

[21] Appl. No.: 899,335

[22] Filed: Aug. 22, 1986

Related U.S. Application Data

[63] Continuation-in-part of Ser. No. 677,738, Dec. 3, 1984, abandoned, which is a continuation-in-part of Ser. No. 519,129, Aug. 1, 1983, abandoned.

[51] Int. Cl.$^4$ ..................... C09F 5/00; C07C 103/34; C07C 87/30; C07C 85/00
[52] U.S. Cl. ................................ 260/404.5; 562/564; 564/197; 564/295; 564/296; 564/292
[58] Field of Search ................. 260/404.5 Q; 562/564; 564/197, 295, 296, 292

[56] References Cited

U.S. PATENT DOCUMENTS 3,642,663 2/1972 Greer .................................. 564/295
4,480,126 10/1984 Rutzen ............................... 564/296

OTHER PUBLICATIONS

McKelvey et al, *Industrial and Engineering Chemistry*, Product & Research Development, 6(2), pp. 115–120, (1967).

Primary Examiner—Charles F. Warren
Assistant Examiner—Elizabeth A. Hanley
Attorney, Agent, or Firm—Irwin M. Stein

[57] ABSTRACT

A method of preparing certain bis-quaternary ammonium compounds and mixtures is disclosed. The method involves contacting a tertiary amine with a suitable amount of neutralizing acid, e.g. HCl, and subsequently contacting the resulting mixture with a suitable epoxide, e.g. epichlorohydrin, at an elevated temperature and in an amount that e.g. 2-hydroypropylene-bis-1,3-(dimethyl stearyl ammonium chloride) is obtained in almost stoichiometric yields. The resulting bis-quaternary ammonium compounds can be incorporated into a hair conditioner whereby a softer feel and better control of hair is obtained.

The general structure for the resulting bis-quaternary ammonium compounds is as follows:

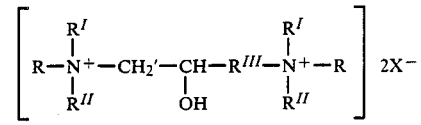

wherein the R's are selected from the group consisting of alkyl, alkylamidoalkyl, aryalkyl, aryl, alkoxy, alkenyl, hydroxyalkyl, and carboxyalkyl and X is a negative radical from the epoxide used, e.g. epichlorohydrin.

22 Claims, No Drawings

PROCESS FOR THE MANUFACTURE OF BIS-QUATERNARY AMMONIUM COMPOUNDS

This application is a continuation-in-part of applicant's U.S. patent application Ser. No. 677,738, filed 12/03/84, abandoned, which in turn was a continuation-in-part of applicant's U.S. patent application Ser. No. 519,129, dated Aug. 1, 1983, now abandoned.

BACKGROUND OF THE INVENTION

1. Field of Invention

The present invention relates to a process for preparing certain bis-quaternary ammonium compounds and mixtures thereof. the present invention also relates to improved hair conditioners, skin lotions and other similar cosmetic compositions. Further, the present invention relates to novel bis-quaternary ammonium compounds.

2. Description of the Prior Art

Several examples of bis-quaternary or poly-quanternary ammonium compounds have appeared in the patent and trade literature. U.S. Pat. No. 2,129,264 describes the condensation of "glycerol-di-chlorhydrine" with a tallow dimethyl amine to form a "di-quanternary" ammonium salt. U.S. Pat. No. 2,944,902 describes the conversion of polyethylene glycols with methanesulfonyl chloride to the corresponding bis-ester. Condensation of the bis-ester with a tertiary amine results in the bis-quaternary ammonium salt. U.S. Pat. No. 3,349,032 describes the use of alkylene dihalides or the conversion of bis-tertiary amines with monomeric alkylating agents to bis-quaternary ammonium compounds. U.S. Pat. No. 3,954,633 illustrates the quaternization of tertiary fatty diamines which were prepared from fatty amines by the cyanoethylation route. U.S. Pat. No. 4,110,263 and U.S. Pat. No. 4,181,634 describe the conversion of polyalkylene glycols into bis-$\alpha,\omega$-bromoderivatives with phosphorus tribromide and subsequent conversion into the desired bis-quaternary ammonium bromide.

Epichlorohydrin has been employed in a variety of reactions designed to generate quaternary ammonium compounds. For example, U.S. Pat. No. 2,129,264 describes the reaction of fatty tertiary amines and epichlorohydrin to afford mono-quaternary ammonium derivatives. It is also known that secondary amines will condense with epichlorohydrin to form polymeric quaternary ammonium compounds.

Recently a paper was presented before the Society of Cosmetic Chemists (Robert J. Verdicchio, annual meeting; May 13, 1982, Memphis, Tenn.) describing the exceptional affect of certain bis-quaternary ammonium salts on the eye irritation of various cosmetic detergent formulations. It has been shown that the described "bis-quats" act as counter irritants. U.S. Pats. Nos. 4,110,263 and 4,181,634 describe this effect in greater detail.

SUMMARY OF THE INVENTION

The present invention is a process for the direct synthesis of bis-quaternary ammonium compounds of which 2-hydroxypropylene-bis-1,3-(dimethyl stearyl ammonium chloride) is an example. The process involves contacting a tertiary amine with a suitable amount of neutralizing acid, such as HCl, whereby about half of the tertiary amine is neutralized, producing a solution with approximately equimolar concentrations of tertiary amine and tertiary amine salt. The process further involves contacting the resulting mixture with an approximately equimolar amount of a suitable epoxide such as epichlorohydrin, so that approximately equimolar amounts of tertiary amine, tertiary amine salt and epoxide are used, at an elevated temperature, such that, for example, 2 hydroxypropylene-bis-1, 3-(dimethyl stearyl ammonium chloride) is obtained in almost stoichiometric yields. Modifications of the process are also disclosed. The resulting bis-quaternary ammonium compounds have utility as an additive to cosmetics, such as a hair conditioner, whereby a softer feel and better control of the hair is obtained.

DESCRIPTION OF THE INVENTION

Schematically, the present invention can be visualized by the following reaction steps:

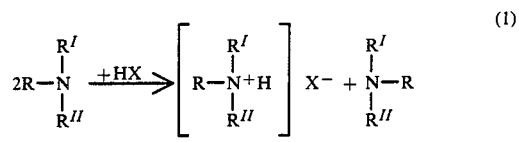
(1)

wherein the R's are defined hereinafter and wherein HX is selected from a neutralizing acid in which, for example, X is F, Cl, Br, NO$_3$, CH$_3$SO$_3$, and CH$_3$C$_6$H$_4$SO$_3$; a mixture of different neutralizing acids can be used; and

(2)

Step 1

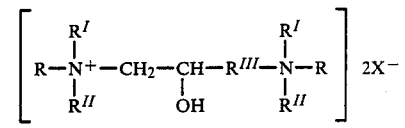

wherein R, $R^I$, $R^{II}$, and $R^{III}$ each are selected from the group consisting of alkyl, alkylamidoalkyl, arylalky, aryl, alkoxy, alkenyl, hydroxyalkyl, and carboxyalkyl, each having 1-28 carbon atoms and X is a negative radical or a radical obtained from the neutralizing acid and/or the epoxide. Preferably $R^I$ and $R^{II}$ are C$_6$–C$_{28}$ alkyl groups. The epoxide used in reaction 2 can be represented by the following graphic formula or structure

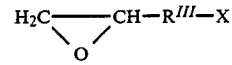

and X is a negative radical which is either the same or different from the X of the neutralizing radical of the acid. Preferred epoxides are epihalohydrins of which epichlorohydrin and epibromohydrin are most preferred. Mixtures of various epoxides can be used.

Step I, which involves contacting the tertiary amine having the aforementioned structure with an amount of neutralizing acid whereby about half of the tertiary amine is neutralized, produces a solution with approximately equimolar concentrations of tertiary amine and tertiary amine salt. Step II involves contacting the resulting mixture of Step I with an approximately equimolar amount of an epoxide having the aforementioned structure so that approximately equimolor amounts of tertiary amine, tertiary amine salt and epoxide are used.

A consideration of the chemistry of steps 1 and 2 revolves around the reactivity of the selected tertiary amine. It must be a strong enough nucleophile to be readily alkylated. When the R's of equation 1 are aliphatic and contain no electron withdrawing groups or excessive steric hindrance, the reaction proceeds readily through steps 1 and 2. Examples of the preferred reactive tertiary amines are found in the fatty dimethyl amine species. These are represented, for example, as follows:

wherein
x is an interger of from 1 to 6,
R is an alkyl group containing 1 to 28 carbon atoms, and
$R_I$ is an alkyl group containing 1 to 4 carbon atoms.

The fatty dialkylamines can be prepared by the reductive amination of fatty acids followed by subsequent conversion to the tertiary amines with formaldehyde and hydrogen in the presence of a catalyst such as Raney Nickel, or by the conversion of alpha olefins to bromo derivatives subsequently condensed with secondary amines, or by the direct conversion of fatty alcohols in the presence of secondary amines and a catalyst.

The alkyl amidoamines are readily prepared from fatty acids and dimethylaminopropylamine through a condensation reaction. Those skilled in the art will realize that fatty esters, acid chlorides, anhydrides and so forth will also produce amido amines.

If amines are chosen that are difficult to alkylate with, for example, benzyl chloride, then it is possible such amines will fail to perform in this reaction. The chemistry of benzylation of tertiary amines is well known to the art; therefore, those skilled in the art of quaternization can determine whether or not a candidate tertiary amine can be quaternized by benzyl chloride or by the instant invention without undue effort.

The monofunctional acid used to neutralize one half of the tertiary amine functionality must be selected from acids that form counter ions ons that will not compete with the said tertiary amine upon subsequent alkylation. For example, acetic acid would not be as ideal as hydrochloric acid because the acetate ion is a much better nucleophile than the chloride ion. Therefore, if the acetate was added to the halohydrin or a reactive intermediate, it would prevent conversion to the quaternary compound.

Suitable neutralizing acids react with the tertiary amine to afford only neutralization. Obviously, acids that caused oxidation or reduction would not be suitable if they destroyed the nature of the other reactants.

Suitable neutralizing acids therefore could be experimentally determined without undue effort by actually trying them in the instant invention. For example, it is known that phosphoric and boric acids or their salts can readily add to epichlorohydrin. Therefore, utility of such acids is questionable. Hydrochloric and methanesulfonic acids for example are acceptable. Other acids can be identified according to the above directions that will also function acceptably.

It is preferred to neutralize about one half of the tertiary amine functionality; otherwise conversion to the bis-quat will not be complete. Either the chlorohydrin (A) or the glycidyl ether (B) would predominate. The glycidyl ether could hydrolyze to the diol (C) with termination of conversion to the bis-quat. This proposed reaction mechanism is illustrated as follows:

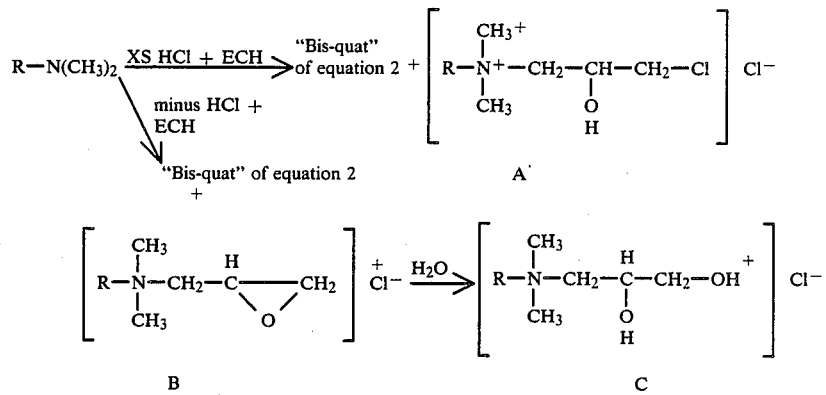

Many of the "bis-quats" formed from fatty dimethyl amines are viscosity builders in water. The $C_{18}$ analog will gel water at as low a concentration as 1%. The reason for this could be the interaction of the two long fatty chains which can form a crosslinked (by Van der Waals forces) three dimensional structure. As expected, monomeric ingredients compatible with the "bis-quats" can readily reduce the vicosity of such mixtures. Therefore, it is preferred that to prepare the "bis-quats" it be done in water, a semi-polar liquid or in a semi-polar liquid-water mixture. Examples of semi-polar liquids include the alcohols such as methanol, ethanol, propanol, isopropanol, butanol, isobutanol, ethylene glycol and propylene glycol. Other alcohols and other classes of solvents compatible with water may be employed. Thus, a general solvent used is one in which the amine, the neutralized amine, the epoxide, and the bis-quaternary ammonium product are soluble. Those skilled in the art of carrying out quaternizations realize that the list of suitable solvents and solvent combinations can be determined experimentally without undue effort.

As in many quaternization reactions some hydrolysis will occur; therefore, although all ingredients are exactly weighed and charged, there is a need at the end of the reaction to adjust the preparations into the required specifications by small additions of epoxide and/or neutralizing acid. If mischarged, and too much hydrolysis has occurred to form the di-hydroxy derivatives (C)

then the preparation cannot be brought into specifications; however, if the chlorohydrin (A) predominates then more tertiary amine can be added to complete the reaction.

If a mixed "bis-quat" is desired, one tertiary amine can be selectively converted into the chlorohydrin (A) followed by condensation with the other tertiary amine. This procedure requires another step but can be carried out in the same reactor. A more detailed analysis to determine conversion to the chlorohydrin (A) is required; however, such mixed products are very desireable because of the ability to design duo-function quaternaries.

For example, a mixed "bis-quat" of lauryl and stearyl dimethyl amines would afford a product in which one quat, the stearyl based compound would afford substantivity to hair or fiber while the lauryl based compound would afford a modest measure of germicidal activity. A greater level of germicidal activity might be expected from a decyl or octyl based diethylamine or greater softening and substantivity would be expected from a larger chain then stearyl.

Simply mixing the amines from the beginning of the process would result in a statistical distribution of the single amine generated "bis-quats" and a portion of the mixed "bis-quats". If a majority of the mixed "bis-quats" is required, then the appropriate chlorohydrin (A) will have to be formed first. Such a refinement does not however require more equipment for manufacture. It is simply two processing steps in one reactor.

Thus, the present invention is a process for preparing bis-quaternary ammonium compounds involving the following. A tertiary amine, as defined herein, is contacted with an amount of a neutralizing acid, as defined herein, which will neutralize about half of the tertiary amine. While neutralizing about half of the tertiary amine is preferred and the more closer the process comes to the one-half the more preferred the process is because of the economics of manufacturing, other amounts of neutralization are within the embodiment of the present invention. A preferred method of contacting is by dissolving the tertiary amine in a suitable solvent as defined herein.

The resulting mixture containing the neutralized tertiary amine is contacted with a suitable epoxide as defined herein. If this contacting is performed with the resulting mixture and a solvent, then the contacting temperature is from about 20° C. to 150° C. A preferred range is from about 50° C. to 100° C. Generally, the epoxide would be slowly added to the resulting mixture.

Another embodiment of the present invention is a process for preparing a mixture of bis-quaternary ammonium compounds involving the following. A tertiary amine,

wherein $R^I$, $R^{II}$ and $R^{III}$ each are selected from the group consisting of alkyl, alkylamidoalkyl, arylalkyl, aryl, alkoxy, alkenyl, hydroxyalkyl and carboxyalkyl and each having 1–28 carbon atoms, is contacted with an amount of neutralizing acid, as defined herein, which will neutralize a substantial portion of the tertiary amine. By substantial is meant that which is desirable depending on the desired composition of the final product. A preferred embodiment is that essentially all of the tertiary amine is neutralized. After the neutralization the resulting neutralized reaction mixture is contacted with an epoxide having the structure

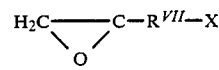

wherein both $R^{VII}$ and X are as defined herein. The contacting temperature of the epoxide and neutralized mixture is in the range from about 20° C. to about 150° C., preferably 50° C. to 100° C. The resulting mixture of the epoxide and neutralized mixture is then subsequentially contacted with a tertiary amine

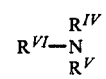

wherein $R^{VI}$, $R^{IV}$ and $R^V$ each are selected from the group consisting of alkyl, alkylamidoalkyl, arylalkyl, aryl alkoxy, alkenyl, hydroxyalkyl and carboxyalkyl, and each having 1–28 carbon atoms and at least one of the R's is different from one of the R's of the tertiary amine contacted with the neutralizing acid. The resulting products from the process for preparing a mixture of bis-ammonium compounds have the following graphic formula or structure:

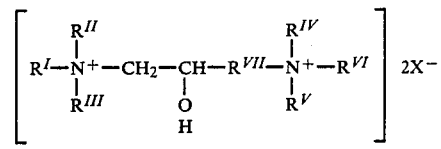

where X is a negative radical or radicals obtained from neutralizing acid and epoxide. Thus, for example, if nitric acid is used to neutralize the amine and an epoxide having a chloride is used to react with the neutralized amine then the X in the above structure is both $NO_3$ and Cl. However, if hydrochloric acid is used to neutralize the amine in place of the nitric acid then the X is Cl.

With either of the above described processes the novel bis-quaternary ammonium compound has the following structure:

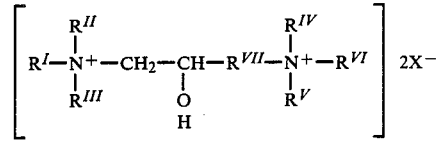

wherein $R^I$, $R^{II}$, $R^{III}$, $R^{IV}$, $R^V$, $R^{VI}$ and $R^{VIII}$ each are selected from the group consisting of alkyl, alkylamidoalkyl, arylalkyl, aryl, hydroxyalkyl and carboxyalkyl each having 1–28 carbon atoms. and X is a negative radical as defined herein. The preferred compounds are wherein $R^{VII}$ has 2–28 carbon atoms.

The "bis-quats" can be considered as useful in many applications. For example, as softeners for various textile and laundry applications, "bis-quats" of stearyl dimethylamine and mixed "bis-quats" of lauryl and stearyl dimethylamines were found to afford similar feel (hand) and acceptable scorch resistance as compared to a variety of commercial softeners. In addition, the phenol coefficients for bacteriocidal effectiveness suggest that the 12/18 "bis-quat" could also function as a bacteriostat, thereby affording the key ingredient in softener/sanitizer formulations. Example 4 illustrates this work.

Hair conditioning in the after shampoo hair care market is another application for the "bis-quats". Preliminary screening on human hair swatches indicate positive conditioning results with the stearyl based "bis-quat".

The "bis-quats" are useful also as antistats, cationic emulsifiers, ore-flotation agents, dye bath assistants, and pigment dispersants, as well as other applications.

The following examples illustrate the invention, but are not to be construed as limiting:

EXAMPLE 1

2-hydroxypropylene-bis-1, 3-dimethyl stearyl ammonium chloride

A 12 liter round bottom flask equipped with a mechanical stirrer, thermometer, reflux condenser and dropping funnel was charged with 2,824 grams of stearyl dimethyl amine (equivalent weight 297); 1,610 grams of isopropanol and 1,610 grams of deionized water. With agitation, 406 grams of concentrated (37.2%) hydrochloric acid was slowly added. After 15 minutes, a sample was removed and analyzed for free amine and aminehydrochloride. In this particular case, employing acid/base titration, a difference of 0.15 meg/g in favor of the amine was observed. Neutralization of half of the residual free amine was desired. This required an additional 51 grams of concentrated hydrochloric acid.

Epichlorohydrin (438 grams) was charged into a pressure equalizing dropping funnel; the mixture was heated to 55° C. and the epichlorohydrin was added dropwise to the mixture over a 1.5 hour period. the temperature rose through a modest exotherm to 85° C. Analysis at this point indicated 3.2% amine hydrochloride and 5.2% free amine. On standing overnight, analysis indicated 1.98% amine hydrochloride and 2.5% free amine. The amine hydrochloride value was employed to calculate an addition of epichlorohydrin. A total of 39 more grams were added dropwise at 70° C. and the mixture agitated an additional four hours. Final analysis was as follows:

Activity (Epton Titration): 46.9% (Equivalent weight 361.5)
% Free Amine: 0.83 (Equivalent weight 297)
% Amine HCl: 0.53 (Equivalent weight 333.5)
% Solids (2 hrs. 150° C.): 51.1
pH (1% aqueous soln): 5.1

Upon standing at ambient temperatures, the clear yellow liquid solidified into a white paste.

EXAMPLE 2

2-hydroxypropylene-bis-1, 3-dimethyl lauryl ammonium chloride

A three liter round bottom flask equipped as above was charged with 461 grams of lauryl dimethyl amine (equivalent weight 218), 299 grams of isopropanol and 233 grams of deionized water. With stirring, 96.8 grams of hydrochloric acid were slowly added. Analysis by acid-base titration indicated an equivalent of free amine and amine hydrochloride to be present. The mixture was heated to 80° C., and 98 grams of epichlorohydrin was slowly charged over an hour and a half. After 8–10 hours of mixing at 80° C., analysis indicated:

% Solids (105° C., 1.5 Hours): 52.0
% Actives (Epton: equivalent weight 265) 43.5
% Free Amine (equivalent weight 218): 0.88
Amine Hydrochloride (equivalent weight 254.4): 0.32

EXAMPLE 3

Mixed bis-quat of Lauryl dimethyl amine and Stearyl dimethyl amine

A three liter round bottom flask equipped as above was charged with 422 grams of lauryl dimethyl amine, 563 grams of iospropanol alcohol and 501 grams of deionized water. With agitation, 185 grams of concentrated 37% hydrochloric acid was added. This addition raised the temperature to 80° C. At this point, 175 grams of epichlorohydrin was added over a ½ hour period. Analysis indicated acceptable conversion to the quat-halohydrin chloride salt. To this mixture was added 577 grams of stearyl dimethyl amine. The mixture was reacted out at 80° C. for 8–10 hours. In order to bring the free amine and amine HCl into specification, an additional 15 grams of epichlorohydrin was required. Final analysis was as follows:

% Solids (105° C., 1.5 hrs.): 52.9
% Actives (equivalent weight 319.5): 46.8
% Amine HCl (equivalent weight 291.5): 0.9
% Free Amine (mw 255): 1.1
pH (10% Aq soln): 6.8

EXAMPLE 4

2-hydroxypropylene-bis-1,3-stearamidopropyldimethyl-ammonium chloride

A three liter round bottom flask equipped as above was charged with 394 grams of stearamidopropyl dimethyl amine (equivalent weight 365), 500 grams isopropanol and 500 grams deionized water. To this, with agitation, was added 54.9 grams concentrated HCl. The mixture was heated to 80° C. and 103.9 grams of epichlorohydrin was added over a ½ hour period. After 8–10 hours at 80° C., the product analyzed as follows:

% Solids (105° C., 1.5 hrs.): 34.1
% Actives (equivalent weight 429.5): 30.1
% Amine HCl (equivalent weight 401.5): 0.1
% Free Amine (equivalent weight 365): 0.3

EXAMPLE 5

The products of examples 1–3 were evaluated as germicides by the AOAC Phenol Coefficient method against *Staphylococcus aureus* and *Pseudomonas aeruginosa* with the following results:

| Example | S. aureus | Phenol Coeff. P. aeruginosa |
| --- | --- | --- |
| 1 | 45 | 17 |
| 2 | 500 | 133 |
| 3 | 338 | 71 |

Examples 1 and 3 were further evaluated against a variety of textile dye bath softeners and "Downy" on acrylic and polycotton fabric at equal add on concentrations. Subjective results reviewed by a panel of 3–4 individuals identified examples 1 and 3 to be as effective as the commercial products in softening ability.

EXAMPLE 6

A hair conditioner was prepared. The composition was as follows:

| Ingredient | % By Weight |
| --- | --- |
| 2 hydroxypropylene-bis-1, 3-(dimethyl stearylammonium chloride) | 5.0 |
| cetyl alcohol | 2.0 |
| hydroxyethyl cellulose | 2.0 |
| preservation | 0.2 |
| water | Balance |
| Total | 100% |

The procedure used to prepare the hair conditioner was as follows. The hydroxyethyl cellulose was slowly added to cold water with agitation. After mixing the resulting mixture for a sufficient amount of time, it was heated to the range from about 80° C.–90° C. The bis-compound was added to the heated mixture. The cetyl alcohol was melted and added to the heated mixture. The pH of the resulting mixture was adjusted to the range of between from 5.0–6.0 with a 50% solution of citric acid. Perfume may be added as desired.

The above composition was panel tested versus an equivalent formula containing the most widely utilized hair conditioner ingredient, stearalkonium chloride. The formula was adjusted to contain an equal level of active conditioner. The results are as follows:

|  | % Preference for Above Composition | % Preference Stearalkonium Chloride | % Equal |
| --- | --- | --- | --- |
| Overall | 83 | 8 | 9 |
| Wet Combining | 44 | 0 | 56 |
| Dry Combining | 22 | 0 | 78 |
| Body | 40 | 30 | 30 |
| Flyaway | 60 | 0 | 40 |
| Luster | 67 | 0 | 33 |
| Feel | 80 | 10 | 10 |

The comment most often received was that the above composition resulted in a softer feel and better control of the hair than with the stearalkonium chloride.

EXAMPLE 7

A skin lotion was prepared. The composition was as follows:

| INGREDIENTS | % BY WEIGHT |
| --- | --- |
| PORTION A | |
| Glycerol Monostearate | 2.00 |
| Cetyl Alcohol | 0.25 |
| Stearyl Alcohol | 0.25 |
| Isopropyl Palmitate | 4.00 |
| Lanolin | 2.00 |
| Mineral Oil | 8.00 |
| PORTION B | |
| Stearamine Oxide | 10.00 |
| 2 hydroxypropylene-bis-1, 3-(dimethyl stearylammonium chloride) | 4.00 |
| Water | 71.00 |
| PORTION C | |
| Perfume (if desired) | 0.20 |

The procedure used to prepare the skin lotion was as follows. The ingredients of Portion A were blended together and heated to 70° C. with agitation. Each of the ingredients of Portion B were heated separately to 75° C. The stearamine oxide and water were mixed together and the pH of the resulting mixture was adjusted to between from 5.5 to 6.0 by the addition of citric acid. Portion B was blended into Portion A with rapid agitation and while cooling to 35° C., stirred, and at which temperature the perfume, if desired, is generally added.

The above formula was panel tested versus the same composition without the bis-compound. The addition of the latter resulted in better initial and after feel.

The above composition was also panel tested versus a leading national brand. The composition containing the bis-compound was overwhelmingly preferred.

Other "bis-quats" can be prepared in a similar manner as described in Examples 1, 2, 3 and 4 using other epoxides and other tertiary amines with equally good yields.

What is claimed is:

1. A process for preparing bis-quaternary ammonium compounds comprising:
   (a) Contacting a tertiary amine represented by the following graphic formula:

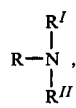

wherein R, $R^I$ and $R^{II}$ are defined hereinafter, with an amount of neutralizing acid sufficient to neutralize about half of the tertiary amine in a solvent selected from the group consisting of water, a semi-polar liquid and a mixture of water and a semi-polar liquid, thereby producing a reaction mixture with approximately equimolar concentration of tertiary amine and tertiary amine salt; and
   (b) Contacting the reaction mixture of step (a) with an approximately equimolar amount of an epoxide represented by the following graphic formula:

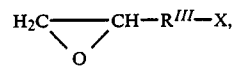

wherein $R^{III}$ and X are defined hereinafter, such that approximately equimolar amounts of tertiary amine, tertiary amine salt and epoxide are used, at temperatures in the range of from about 50° C. to 100° C., whereby to produce as the principal product a bis-quaternary ammonium compound represented by the following graphic formula:

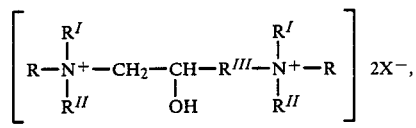

wherein R, $R^I$, $R^{II}$ and $R^{III}$ are each selected from the group consisting of alkyl, alkylamidoalkyl, aryl, alkoxy, alkenyl, arylalkyl, hydroxyalkyl and carboxyalkyl having from 1 to 28 carbon atoms and wherein X is a negative radical or radicals obtained from the group consisting of the neutralizing acid and epoxide.

2. The process of claim 1 wherein the semi-polar liquid is selected from the group consisting of methanol, ethanol, propanol, isopropanol, butanol, isobutanol, ethylene glycol and propylene glycol.

3. The process of claim 1 wherein the neutralizing acid is selected from the group consisting of hydrofluoric, hydrochloric, hydrobromic, nitric, methanesulfonic and toluenesulfonic acids.

4. The process of claim 1 wherein the epoxide is an epihalohydrin.

5. The process of claim 4 wherein the epihalohydrin is epichlorohydrin.

6. The process of claim 1 wherein the negative radical, X, is selected from chlorine and bromine.

7. The process of claim 1 wherein $R^I$ and $R^{II}$ are a $C_6$-$C_{28}$ alkyl.

8. The process of claim 1 wherein the tertiary amine is a dimethyl amine represented by the formula, $R-N(CH_3)_2$, wherein R is an alkyl group containing from 1 to 28 carbon atoms.

9. The process of claim 8 wherein the tertiary amine is selected from stearyl dimethyl amine, lauryl dimethyl amine and mixtures of such tertiary amines.

10. The process of claim 8 wherein the epoxide is epichlorohydrin, the neutralizing acid is hydrochloric acid, and the semi-polar liquid is selected from the group consisting of methanol, ethanol, propanol, butanol, isobutanol, ethylene glycol and propylene glycol.

11. A process of claim 9 wherein the epoxide is epichlorohydrin, the neutralizing acid is hydrochloric acid, and the semi-polar liquid is selected from the group consisting of methanol, ethanol, propanol, butanol, isobutanol, ethylene glycol and propylene glycol.

12. The process of claim 1 wherein the tertiary amine has the following graphic formula:

wherein x is an integer of from 1 to 6, R is an alkyl group having 1 to 28 carbon atoms and $R_I$ is an alkyl group having 1 to 4 carbon atoms.

13. A process for preparing bis-quaternary ammonium compounds comprising:
(a) contacting a tertiary amine represented by the following graphic formula:

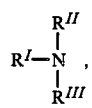

wherein $R^I$, $R^{II}$ and $R^{III}$ are each selected from the group consisting of alkyl, alkylamidoalkyl, arylalkyl, aryl, alkoxy, alkenyl, hydroxyalkyl and carboxyalkyl having from 1 to 28 carbon atoms, with an amount of neutralizing acid sufficient to neutralize a substantial portion of the tertiary amine in a solvent selected from the group consisting of water, a semi-polar liquid and a mixture of water and a semi-polar liquid.

(b) contacting the resulting mixture of step (a) with an epoxide represented by the graphic formula:

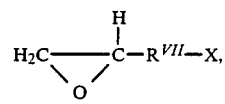

wherein $R^{VII}$ is selected from the group consisting of alkyl, alkylamidoalkyl, arylalkyl, hydroxyalkyl, alkoxy, alkenyl and carboxyalkyl having from 1 to 28 carbon and X is as defined hereinafter at temperatures in the range of from about 50° C. to about 100° C., (c) contacting the resulting mixture of step (b) with a tertiary amine represented by the graphic formula:

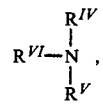

wherein $R^{IV}$, $R^V$ and $R^{VI}$ are each selected from the group consisting of alkyl, alkylamidoalkyl, arylalkyl, aryl, alkoxy, alkenyl, hydroxyalkyl and carboxyalkyl having from 1 to 28 carbon atoms, at least one of $R^I$, $R^{II}$ and $R^{III}$ being different from $R^{IV}$, $R^V$ and $R^{VI}$, whereby to produce as the principal product a mixed bis-quaternary ammonium compound represented by the following graphic formula:

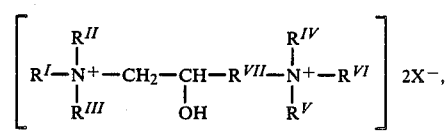

wherein X is a negative radical or radicals obtained from the neutralizing acid and epoxide.

14. The process of claim 13 wherein an amount of neutralizing acid is used to neutralize substantially all of the tertiary amine.

15. The process of claim 13 wherein the neutralizing acid is selected from the group consisting of hydrofluoric, hydrochloric, hydrobromic, nitric, methanesulfonic and toluenesulfonic.

16. The process of claim 14 wherein the neutralizing acid is hydrochloric acid, and the epoxide is epihalohydrin.

17. The process of claim 16 wherein the epoxide is epichlorohydrin.

18. The process of claim 14 wherein the tertiary amine is a dimethyl amine represented by the formula, $R-(CH_3)_2$, wherein R is an alkyl group containing from 1 to 28 carbon atoms.

19. The process of claim 17 wherein the tertiary amine is a dimethyl amine represented by the formula, $R-(CH_3)_2$, wherein R is an alkyl group containing from 1 to 28 carbon atoms.

20. The process of claim 19 wherein the semi-polar liquid is selected from the group consisting of methanol, ethanol, propanol, isopropanol, butanol, isobutanol, ethylene glycol and propylene glycol.

21. The process of claim 16 wherein the semi-polar liquid is selected from the group consisting of methanol, ethanol, propanol, isopropanol, butanol, isobutanol, ethylene glycol and propylene glycol.

22. The process of claim 20 wherein the dimethyl amine is selected from stearyl dimethyl amine and lauryl dimethyl amine.

* * * * *